US012678294B2

(12) United States Patent (10) Patent No.: US 12,678,294 B2
Jung (45) Date of Patent: Jul. 14, 2026

(54) SCREW DRIVING MODULE AND INTERVERTEBRAL FUSION CAGE COMPRISING SAME

(71) Applicant: CG BIO CO., LTD., Seoul (KR)

(72) Inventor: Ui Su Jung, Seoul (KR)

(73) Assignee: CG BIO CO., LTD., Yongsan-Gu (KR)

(*) Notice: Subject to any disclaimer, the term of this patent is extended or adjusted under 35 U.S.C. 154(b) by 79 days.

(21) Appl. No.: 18/697,658

(22) PCT Filed: Sep. 30, 2022

(86) PCT No.: PCT/KR2022/014800
§ 371 (c)(1),
(2) Date: Apr. 1, 2024

(87) PCT Pub. No.: WO2023/055190
PCT Pub. Date: Apr. 6, 2023

(65) Prior Publication Data
US 2024/0407929 A1 Dec. 12, 2024

(30) Foreign Application Priority Data

Oct. 1, 2021 (KR) ........................ 10-2021-0130532
Sep. 29, 2022 (KR) ........................ 10-2022-0124177

(51) Int. Cl.
*A61F 2/44* (2006.01)
*A61F 2/30* (2006.01)
(52) U.S. Cl.
CPC .... *A61F 2/447* (2013.01); *A61F 2002/30405* (2013.01)
(58) Field of Classification Search
CPC .............................. A61F 2/4455–2/447; A61F 2250/0004–2250/001; A61F 2250/0048; A61B 17/8047; A61B 17/8052
See application file for complete search history.

(56) References Cited

U.S. PATENT DOCUMENTS 6,802,680 B1 10/2004 Rubenstein
2014/0277500 A1* 9/2014 Logan ..................... A61F 2/447
623/17.16

(Continued)

FOREIGN PATENT DOCUMENTS

EP 3479799 5/2019
JP 201984358 6/2019

(Continued)

OTHER PUBLICATIONS

International Search Report issued in corresponding International Application No. PCT/KR2022/014800, dated Jan. 9, 2023.

(Continued)

*Primary Examiner* — Julianna N Harvey
(74) *Attorney, Agent, or Firm* — NORTON ROSE FULBRIGHT US LLP

(57) ABSTRACT

A screw driving module and an intervertebral fusion cage including same are disclosed. The screw driving module according to an embodiment of the present invention may comprise: a screw including a screw head and a screw body extending from the screw head and having a screw thread on an outer circumferential surface thereof; a housing in which the screw head is rotatably accommodated; and a threshold torque setting member disposed in the housing and configured to prevent rotation of the screw head when torque is less than a threshold torque set on the screw head and permit rotation of the screw head when torque equal to or greater than the threshold torque is applied.

6 Claims, 12 Drawing Sheets

(56)                References Cited

U.S. PATENT DOCUMENTS

2015/0374507 A1 * 12/2015  Wolters ............. A61B 17/8858
                                           623/17.15
2018/0177603 A1 *  6/2018  Weiman ................. A61F 2/442
2019/0388232 A1 * 12/2019  Purcell .................... A61F 2/442
2021/0236298 A1 *  8/2021  Weiman ................ A61F 2/4611
2022/0395383 A1 * 12/2022  Jung ..................... A61F 2/4601
2023/0190490 A1 *  6/2023  Corrao, Jr. ............ A61F 2/4455
                                           623/17.11

FOREIGN PATENT DOCUMENTS

| KR | 10-2005-0076677 | 7/2005 | |
| KR | 10-2020-0013889 | 2/2020 | |
| KR | 10-2120254 | 6/2020 | |
| KR | 10-2021-0062904 | 6/2021 | |
| KR | 10-2315201 | 10/2021 | |
| WO | WO2021/066524 | 4/2021 | |
| WO | WO-2021066524 A2 * | 4/2021 | ............ A61F 2/4611 |

OTHER PUBLICATIONS

Office Action issued in corresponding Australian Application No. 2022353540, dated Mar. 18, 2025.
Office Action issued in corresponding Japanese Application No. 2024519978, dated Dec. 24, 2024.

* cited by examiner

SCREW DRIVING MODULE AND INTERVERTEBRAL FUSION CAGE COMPRISING SAME

CROSS-REFERENCE TO RELATED APPLICATIONS

This application is a national phase application under 35 U.S.C. § 371 of International Application No. PCT/KR2022/014800, filed Sep. 30, 2022, which claims priority to and the benefit of Korean Application No. 10-2021-0130532, filed Oct. 1, 2021 and Korean Application No. 10-2022-012417710, filed Sep. 29, 2022. The contents of the referenced patent applications are incorporated into the present application by reference in their entireties.

FIELD OF THE DISCLOSURE

The present invention relates to a screw driving module and an intervertebral fusion cage including the same, and more particularly, to a screw driving module and an intervertebral fusion cage including the same that can be applied to an implant requiring expansion in the body.

DESCRIPTION OF RELATED ART

Generally, an implant that requires expansion in the body has a driving system for expansion. A screw driving method is commonly adopted as a driving method of such a driving system. For example, an expansion type intervertebral fusion cage having a structure in which a plate can be displaced upward or downward according to rotation of a screw in the body has been introduced.

Most conventional screw driving structures do not have a separate configuration for preventing loosening of a screw and receive pressure applied to an implant in the body as the only fixing means. Accordingly, in a case where an impact of a certain level or more is applied due to an accident or the like to a patient who has undergone implantation of an implant or continuous fatigue is accumulated on an implant in everyday life of a patient who has undergone implantation of an implant, a problem in which loosening of a screw disturbs an expanded state of an implant may occur. In order to address such a problem, there is a need for development of a structure that prevents loosening of a screw to, after implantation of an implant that is expanded in the body using a screw driving method, stably maintain the expanded state of the implant.

SUMMARY

The present invention is directed to providing a screw driving module and an intervertebral fusion cage including the same in which a mechanical minimum threshold torque is applied to driving of a screw to prevent unintentional loosening of the screw.

Objectives of the present invention are not limited to the above-mentioned objective, and other unmentioned objectives should be clearly understood by those of ordinary skill in the art to which the present invention pertains from the description below.

One aspect of the present invention provides a screw driving module including: a screw including a screw head and a screw body extending from the screw head and having screw threads on an outer circumferential surface thereof; a housing in which the screw head is rotatably accommodated; and a threshold torque setting member disposed in the housing and configured to prevent rotation of the screw head with torque less than a threshold torque set on the screw head and allow the rotation of the screw head in a case where torque greater than or equal to the threshold torque is applied.

In the screw driving module according to one embodiment of the present invention, the screw head may have one or more first grooves on an outer circumferential surface thereof, and while inserted into the first grooves of the screw head, the threshold torque setting member may prevent the rotation of the screw head before the set threshold torque is applied, and in the case where the torque greater than or equal to the threshold torque is applied, the threshold torque setting member may be separated from the first grooves and allow the rotation of the screw head.

In the screw driving module according to one embodiment of the present invention, the first grooves may be formed in a longitudinal direction of the screw.

In the screw driving module according to one embodiment of the present invention, a plurality of the first grooves may be disposed at predetermined intervals in a circumferential direction of the screw head.

In the screw driving module according to one embodiment of the present invention, the threshold torque setting member may include a member body disposed to surround at least a portion of a circumference of the screw head and a catching portion protruding from the member body toward the screw head in order to be inserted into the first grooves.

In the screw driving module according to one embodiment of the present invention, the screw head may further include a second groove continuously recessed in the circumferential direction, and the screw driving module may further include a separation preventing member disposed to be fixed to the housing while inserted into one portion of the second groove and configured to prevent the screw from being separated from the housing.

In the screw driving module according to one embodiment of the present invention, the separation preventing member may be formed in the shape of a pin and may be disposed perpendicular to the screw.

Another aspect of the present invention provides an intervertebral fusion cage including: a screw driving module including a screw including a screw head and a screw body extending from the screw head and having screw threads on an outer circumferential surface thereof, a housing in which the screw head is rotatably accommodated, and a threshold torque setting member disposed in the housing and configured to prevent rotation of the screw head with torque less than a threshold torque set on the screw head and allow the rotation of the screw head in a case where torque greater than or equal to the threshold torque is applied; a guide member to which the screw body of the screw is screw-rotatably coupled; and one or more plates movably connected to the housing and configured to be displaced according to relative movement between the screw driving module and the guide member, wherein, during rotation of the screw, the screw driving module moves forward or rearward relative to the guide member, and the plates are displaced due to the guide member.

In the intervertebral fusion cage according to one embodiment of the present invention, the guide member may have a guide body formed to be vertically penetrated, and the screw driving module may be disposed in the guide body.

In the intervertebral fusion cage according to one embodiment of the present invention, the guide member may have a screw hole formed at a front thereof, and the screw body of the screw may be screw-coupled to the screw hole.

In the intervertebral fusion cage according to one embodiment of the present invention, the guide member may further have a rear hole formed to be penetrated at a rear thereof and communicating with the guide body, and a driving tool passing through the rear hole may be able to reach the screw head.

In the intervertebral fusion cage according to one embodiment of the present invention, the housing may have a first connecting portion formed in a vertical direction, and the plate may have a second connecting portion movably connected to the first connecting portion in the vertical direction.

In the intervertebral fusion cage according to one embodiment of the present invention, the screw head may have one or more first grooves on an outer circumferential surface thereof, and while inserted into the first grooves of the screw head, the threshold torque setting member may prevent the rotation of the screw head before the set threshold torque is applied, and in the case where the torque greater than or equal to the threshold torque is applied, the threshold torque setting member may be separated from the first grooves and allow the rotation of the screw head.

In the intervertebral fusion cage according to one embodiment of the present invention, the first grooves may be formed in a longitudinal direction of the screw.

In the intervertebral fusion cage according to one embodiment of the present invention, a plurality of the first grooves may be disposed at predetermined intervals in a circumferential direction of the screw head.

In the intervertebral fusion cage according to one embodiment of the present invention, the threshold torque setting member may include a member body disposed to surround at least a portion of a circumference of the screw head and a catching portion protruding from the member body toward the screw head in order to be inserted into the first grooves.

In the intervertebral fusion cage according to one embodiment of the present invention, the screw head may further include a second groove continuously recessed in the circumferential direction, and the screw driving module may further include a separation preventing member disposed to be fixed to the housing while inserted into one portion of the second groove and configured to prevent the screw from being separated from the housing.

In the intervertebral fusion cage according to one embodiment of the present invention, the separation preventing member may be formed in the shape of a pin and may be disposed perpendicular to the screw.

In the intervertebral fusion cage according to one embodiment of the present invention, the guide member may further have side guide portions formed at both sidewalls of the guide body in a front-rear direction, and the separation preventing member may be disposed to pass through both sides of the housing and have one end and the other end seated on the side guide portions, respectively.

According to embodiments of the present invention, by a threshold torque setting member applying a mechanical minimum threshold torque to driving of a screw, unintentional loosening of the screw can be prevented in a screw driving module, and by the screw driving module having such a structure, an expansion type intervertebral fusion cage can stably maintain an expanded state after being implanted in the patient's body.

Advantageous effects of the present invention are not limited to those mentioned above and should be understood as including all advantageous effects inferable from the detailed description of the present invention or the configuration of the invention stated in the claims.

BRIEF DESCRIPTION OF THE DRAWINGS

FIG. 3 is a view transparently illustrating a housing of the screw driving module according to one embodiment of the present invention.

FIG. 5 is a perspective view of an intervertebral fusion cage according to one embodiment of the present invention.

FIG. 12 is a perspective view of a state in which a height of the plate of the intervertebral fusion cage according to one embodiment of the present invention is increased after the angle of the plate is expanded.

FIG. 13 is a lateral view of the state in which the height of the plate of the intervertebral fusion cage according to one embodiment of the present invention is increased after the angle of the plate is expanded.

FIG. 14 is a view illustrating a process in which the intervertebral fusion cage according to one embodiment of the present invention is used in posterior lumbar interbody fusion (PLIF).

DETAILED DESCRIPTION OF THE INVENTION

Figure 1:
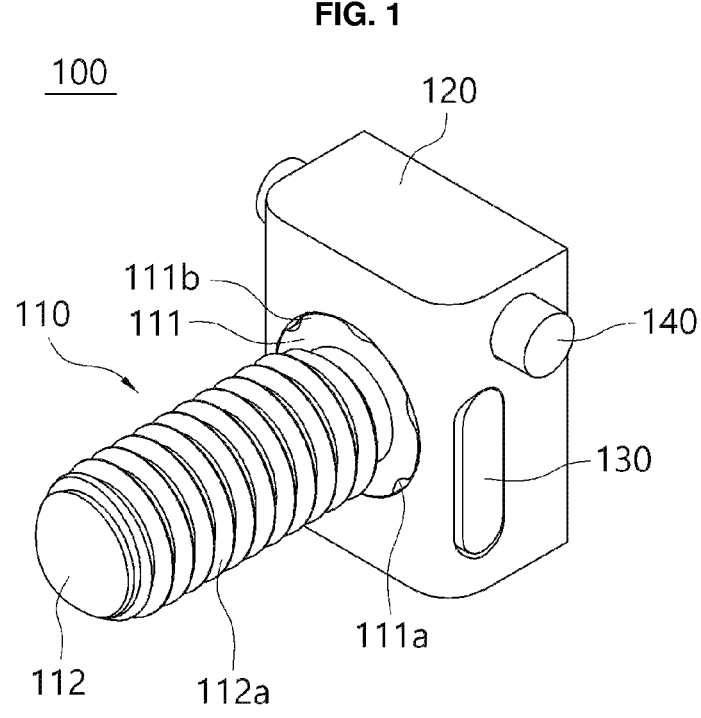
FIG. 1 is a front perspective view of a screw driving module according to one embodiment of the present invention.

Hereinafter, embodiments of the present invention will be described in detail with reference to the accompanying drawings so that those of ordinary skill in the art to which the present invention pertains can easily carry out the present invention. The present invention may be implemented in various different forms and is not limited to the embodiments described herein. In the drawings, in order to clearly describe the present invention, parts irrelevant to the description are omitted, and like or similar components are denoted by like reference numerals throughout the specification.

Words or terms used in the present specification and the claims should not be interpreted as being limited to their general or dictionary meanings and should be interpreted as having meanings and concepts consistent with the technical spirit of the present invention according to the principle that the inventor may define the terms and concepts thereof in order to describe his or her invention in the best possible way.

In the present specification, terms such as "include" or "have" are intended to designate the presence of features, numbers, steps, operations, components, parts, or combinations thereof described herein and should not be understood as precluding the possibility of presence or addition of one or more other features, numbers, steps, operations, components, parts, or combinations thereof.

When a certain component is described as being "in front of," "behind," "beside," "above," or "under" another component, unless there is some special circumstance, this not only includes a case in which the component is disposed right "in front of," "behind," "beside," "above," or "under" the other component, but also includes a case in which another component is disposed between the two components. Also, when a certain component is described as being "connected" to another component, unless there is some special circumstance, this not only includes a case in which the component and the other component are directly connected to each other, but also includes a case in which the component and the other component are indirectly connected to each other.

Hereinafter, a screw driving module according to one embodiment of the present invention will be described with reference to the drawings.

Figure 2:
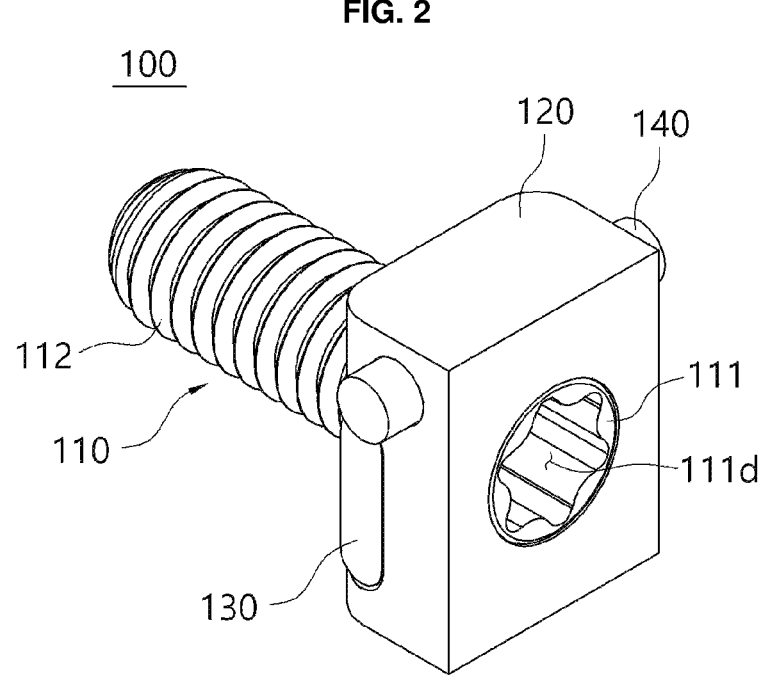
FIG. 2 is a rear perspective view of the screw driving module according to one embodiment of the present invention.
Figure 3:
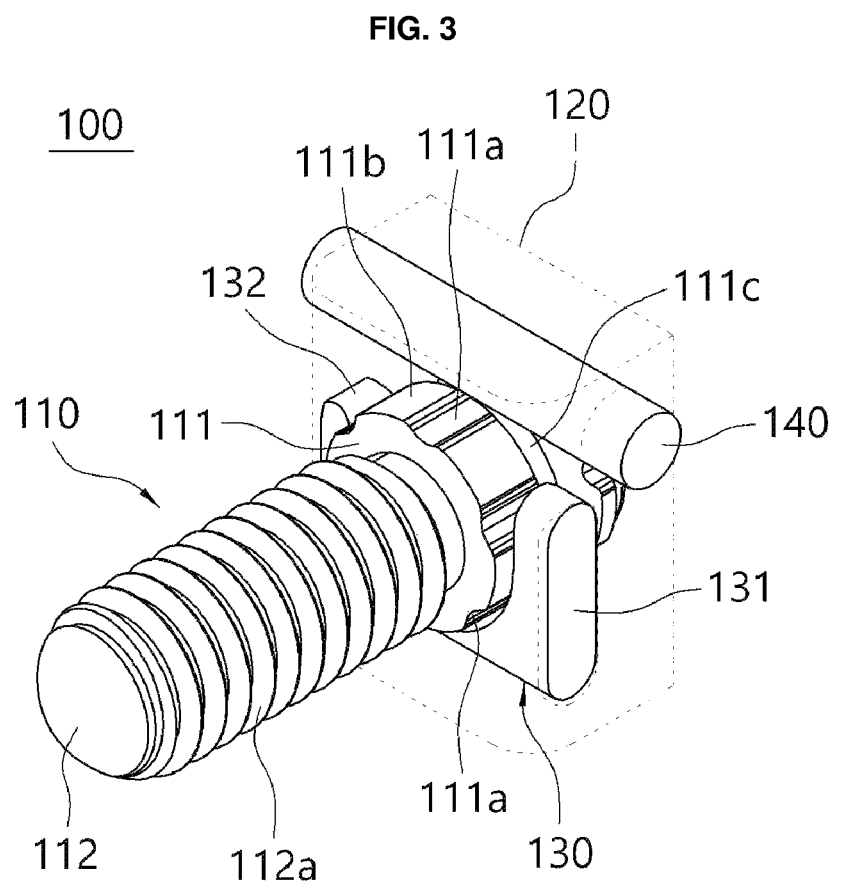
Figure 4:
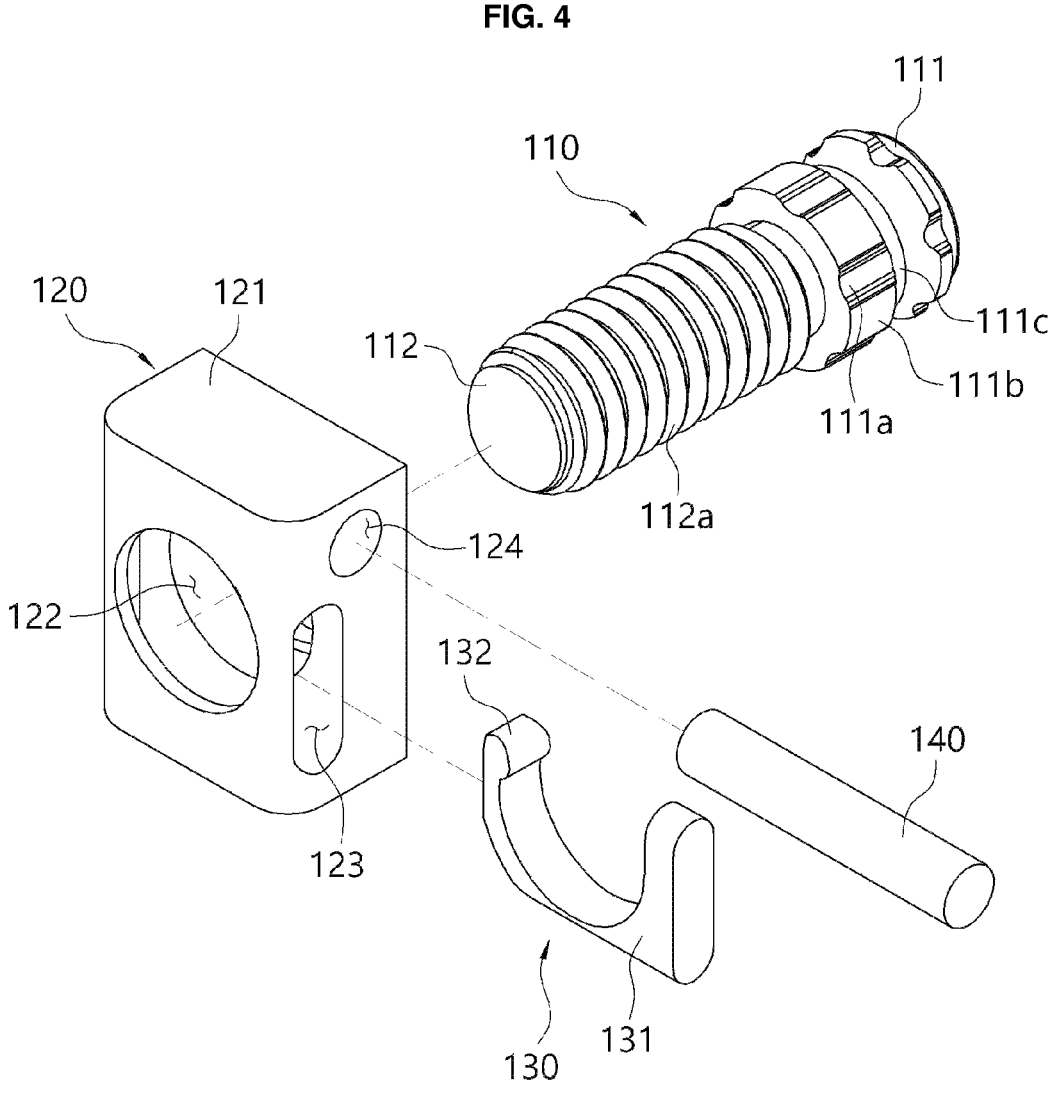
FIG. 4 is an exploded perspective view of the screw driving module according to one embodiment of the present invention.

FIG. 1 is a front perspective view of a screw driving module according to one embodiment of the present invention, and FIG. 2 is a rear perspective view of the screw driving module according to one embodiment of the present invention. Also, FIG. 3 is a view transparently illustrating a housing of the screw driving module according to one embodiment of the present invention, and FIG. 4 is an exploded perspective view of the screw driving module according to one embodiment of the present invention.

A screw driving module 100 according to one embodiment of the present invention provides a driving force according to rotation of a screw. For example, the screw driving module 100 may, during rotation of a screw, move forward or rearward relative to a counterpart engaged with the screw.

Referring to FIGS. 1 to 4, the screw driving module 100 according to one embodiment of the present invention may include a screw 110, a housing 120, a threshold torque setting member 130, and a separation preventing member 140.

The screw 110 includes a screw head 111 and a screw body 112 extending from the screw head 111 and having screw threads 112a on an outer circumferential surface thereof. The screw 110 is rotatably disposed in the housing 120 and is screw-coupled to a counterpart (not illustrated). The housing 120 and the counterpart may move relative to each other so that the housing 120 and the counterpart approach each other or move away from each other in a longitudinal direction of the screw 110 according to rotation of the screw 110.

The screw head 111 has one or more first grooves 111a on an outer circumferential surface thereof. The first grooves 111a may be formed in the longitudinal direction of the screw 110. Also, a plurality of the first grooves 111a may be disposed at predetermined intervals in a circumferential direction of the screw head 111. Also, a first protruding portion 111b protruding radially outward relative to the first grooves 111a is formed between adjacent first grooves 111a.

In one embodiment of the present invention, the screw head 111 may further include a second groove 111c continuously recessed in the circumferential direction. The second groove 111c is formed for the separation preventing member 140 to be inserted thereinto. Meanwhile, the screw head 111 may have a driving tool coupling portion 111d, which is for coupling of a driving tool (not illustrated), disposed at an end in an opposite direction of a portion where the screw body 112 extends.

The screw body 112 is connected to the screw head 111 and has the screw threads 112a on the outer circumferential surface thereof. The screw threads 112a of the screw body 112 are engaged with the counterpart and, during the rotation of the screw 110, transmit a rotational force of the screw to the counterpart. The rotational force of the screw that is transmitted to the counterpart is converted into a driving force for linear displacement between the housing 120 and the counterpart.

The housing 120 rotatably accommodates the screw head 111. The screw body 112 of the screw 110 is screw-coupled to the counterpart (not illustrated), and when rotation of the screw occurs due to the driving tool (not illustrated) coupled to the screw head 111, the housing 120 and the counterpart approach each other or move away from each other.

In one embodiment of the present invention, the housing 120 may include a housing body 121, a screw head arrangement portion 122, a threshold torque setting member arrangement portion 123, and a separation preventing member arrangement portion 124.

The housing body 121 may have various shapes as long as the screw head 111 can be accommodated therein. In one embodiment of the present invention, the housing body 121 may have the shape of a quadrangular box.

The screw head arrangement portion 122 is formed to pass through the housing body 121 in a front-rear direction. Accordingly, in a state in which the screw head 111 is disposed at the screw head arrangement portion 122, the driving tool for rotating the screw head 111 may be coupled to the screw head 111, and the screw body 112 may protrude to the front of the housing body 121.

The threshold torque setting member arrangement portion 123 is formed in the housing body 121 for the threshold torque setting member 130 to be disposed therein. In one embodiment of the present invention, the threshold torque setting member arrangement portion 123 is formed to surround at least a portion of the screw head arrangement portion 122. More specifically, the threshold torque setting member arrangement portion 123 has the shape of a slot passing through both sides of the housing body 121 for the threshold torque setting member 130 to be disposed to pass through a side surface of the housing body 121.

The separation preventing member arrangement portion 124 is formed in the housing body 121 for the separation preventing member 140 to be disposed therein. In one embodiment of the present invention, the separation preventing member arrangement portion 124 is formed as a through-hole passing through both sides of the housing body 121, and at least a portion of the separation preventing member 140 is formed to be inserted into the second groove 111c of the screw head 111.

The threshold torque setting member 130 is disposed in the housing 120, prevents rotation of the screw head 111 with torque less than a threshold torque set on the screw head 111, and allows the rotation of the screw head 111 in a case where torque greater than or equal to the threshold torque is applied. The threshold torque setting member 130 may, while inserted into the first grooves 111a of the screw head 111, suppress the rotation of the screw head 111 before the set threshold torque is applied and may be separated from the first grooves 111a and allow the rotation of the screw head 111 in the case where the torque greater than or equal to the threshold torque is applied.

In one embodiment of the present invention, the threshold torque setting member 130 may include a member body 131 disposed to surround at least a portion of a circumference of the screw head 111 and a catching portion 132 protruding from the member body 131 toward the screw head 111 in order to be inserted into the first grooves 111a. More specifically, the member body 131 may be disposed to surround about half of the screw head 111 in the circumferential direction thereof, and the catching portion 132 may protrude from one side end of the member body 131 toward the screw head 111. The catching portion 132 may, while inserted into the first grooves 111a, limit the rotation of the screw head 111 before the torque greater than or equal to the threshold torque acts on the screw 110, and may be pressed by the first protruding portion 111b adjacent thereto and separated from the first grooves 111a in a case where the torque greater than or equal to the threshold torque acts on the screw 110. In relation to this, in the case where the torque greater than or equal to the threshold torque is applied to the screw 110, the member body 131 may be elastically deformed.

The separation preventing member 140 is disposed to be fixed to the housing 120 while inserted into one portion of the second groove 111c and prevents the screw 110 from being separated from the housing 120. In one embodiment of the present invention, the separation preventing member 140 may be formed in the shape of a pin. More specifically, in a state in which the separation preventing member 140 is inserted into the separation preventing member arrangement portion 124 formed as the through-hole passing through both sides of the housing body 121, at least a portion of the separation preventing member 140 may be inserted into the second groove 111c of the screw head 111. Also, the separation preventing member 140 may be disposed perpendicular to the screw 110.

Figure 5:
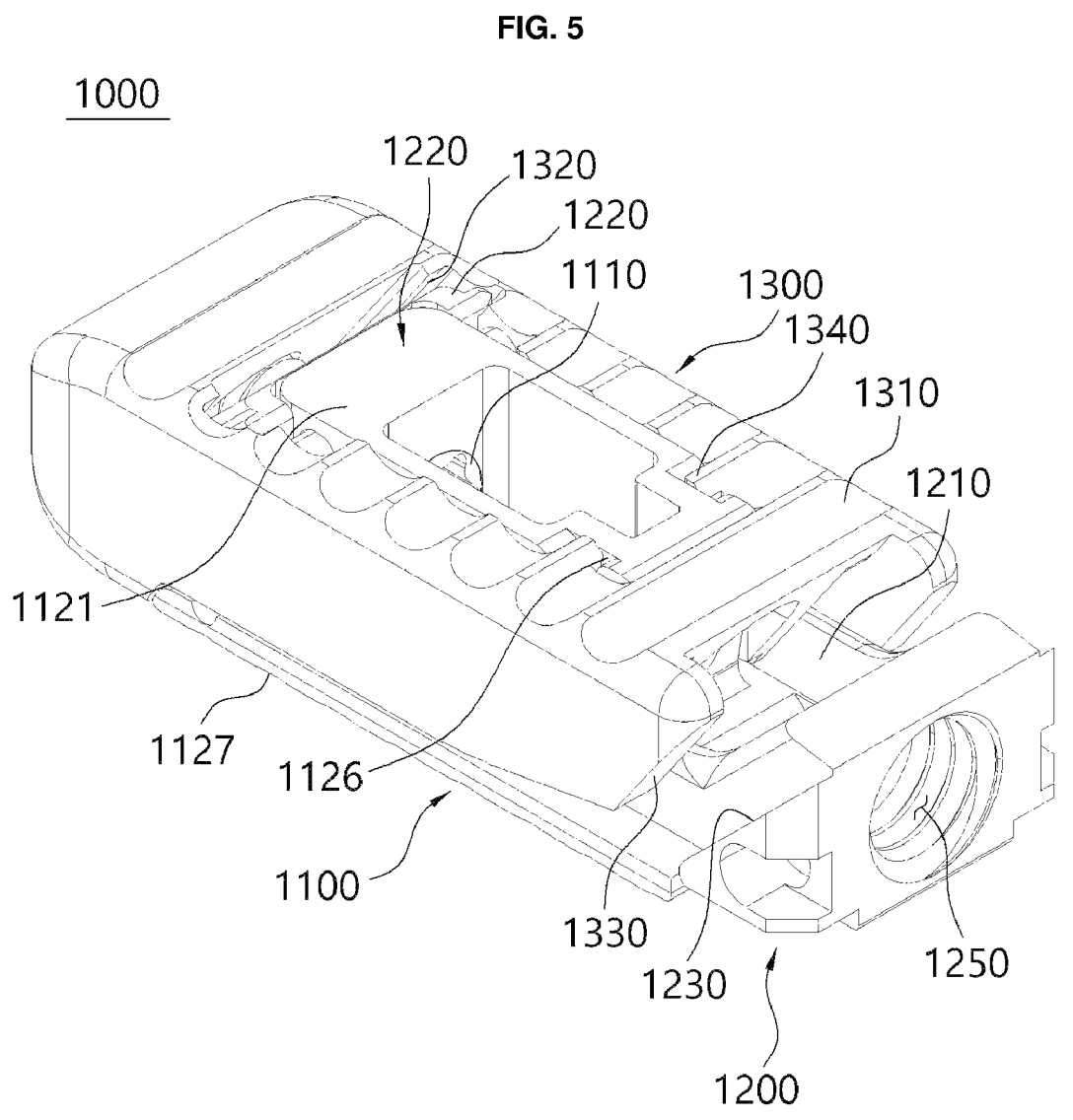
Figure 6:
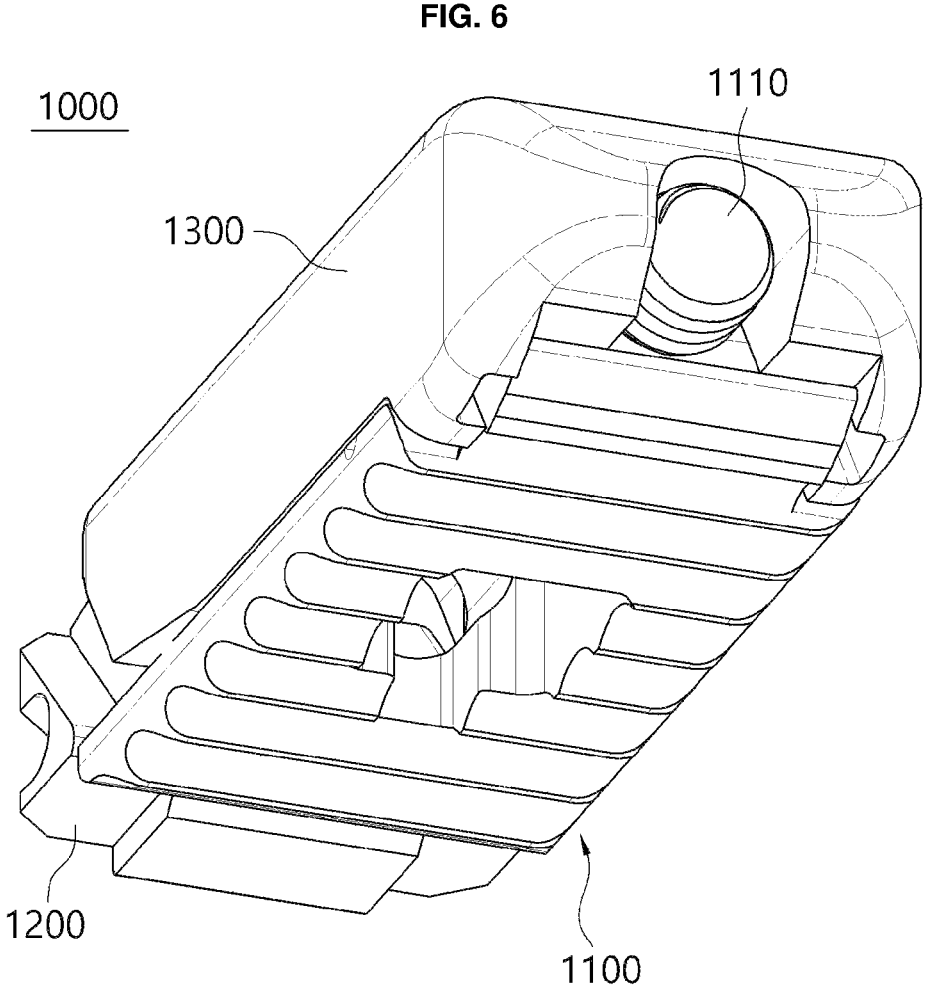
FIG. 6 is a perspective view illustrating the intervertebral fusion cage according to one embodiment of the present invention in another direction.

FIG. 5 is a perspective view of an intervertebral fusion cage according to one embodiment of the present invention, and FIG. 6 is a perspective view illustrating the intervertebral fusion cage according to one embodiment of the present invention in another direction. Also, FIG. 7 is an exploded perspective view of the intervertebral fusion cage according to one embodiment of the present invention.

An intervertebral fusion cage 1000 according to one embodiment of the present invention is a device used in fusion which is a surgical method for treating spinal diseases. The intervertebral fusion cage 1000 according to one embodiment of the present invention includes a screw driving module 1100 as a driving system. Also, the intervertebral fusion cage 1000 according to one embodiment of the present invention is inserted into a portion between vertebrae, from which a degenerative disc has been removed, and serves to support the portion between the vertebrae until spinal fusion is performed. The intervertebral fusion cage 1000 according to one embodiment of the present invention allows both lordosis and height of the spine to be secured.

Figure 7:
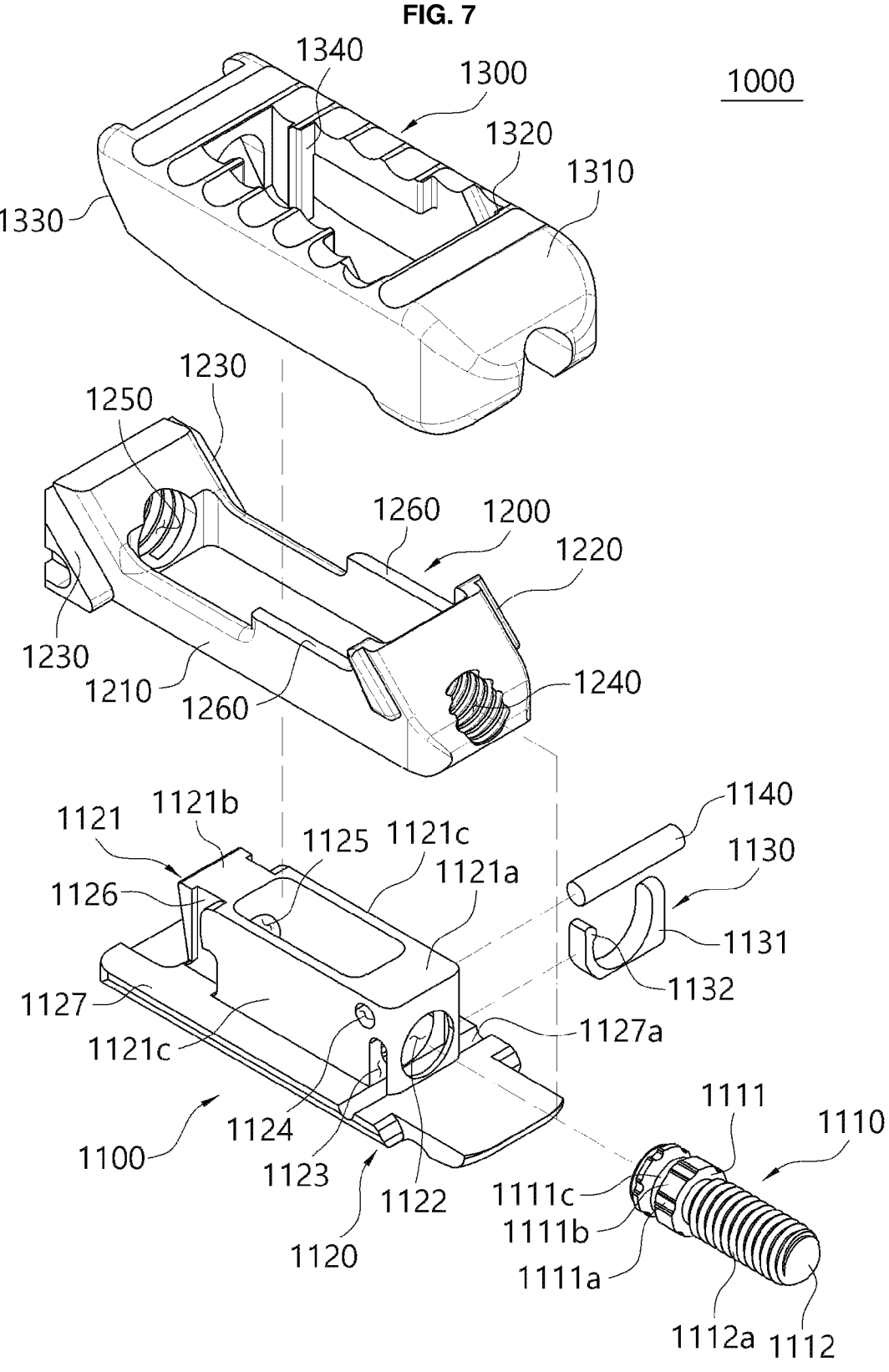
FIG. 7 is an exploded perspective view of the intervertebral fusion cage according to one embodiment of the present invention.

Referring to FIGS. 5 to 7, the intervertebral fusion cage 1000 according to one embodiment of the present invention may include the screw driving module 1100, a guide member 1200, and a plate 1300.

The screw driving module 1100 moves relative to the guide member 1200 according to rotation of a screw 1110 and causes displacement of the plate 1300. The screw driving module 1100 may include the screw 1110, a housing 1120, a threshold torque setting member 1130, and a separation preventing member 1140.

The screw 1110 includes a screw head 1111 and a screw body 1112 extending from the screw head 1111 and having screw threads 1112a on an outer circumferential surface thereof.

The screw head 1111 has one or more first grooves 1111a on an outer circumferential surface thereof. The first grooves 1111a may be formed in the longitudinal direction of the screw 1110. Also, a plurality of the first grooves 1111a may be disposed at predetermined intervals in a circumferential direction of the screw head 1111. Meanwhile, a first protruding portion 1111b protruding radially outward relative to the first grooves 1111a is formed between adjacent first grooves 1111a.

Also, the screw head 1111 may further include a second groove 1111c continuously recessed in the circumferential direction. The second groove 1111c is formed for the separation preventing member 1140 to be inserted thereinto.

The screw body 1112 is connected to the screw head 1111 and has the screw threads 1112a on the outer circumferential surface thereof. The screw threads 1112a of the screw body 1112 are engaged with the guide member 1200 and, during the rotation of the screw 1110, transmit a rotational force of the screw to the guide member 1200. The rotational force of the screw that is transmitted to the guide member 1200 is converted into a driving force for linear displacement between the housing 1120 and the guide member 1200.

The housing 1120 rotatably accommodates the screw head 1111. The screw body 1112 of the screw 1110 is screw-coupled to the guide member 1200, and when rotation of the screw occurs due to a driving tool (not illustrated) coupled to the screw head 1111, the housing 1120 and the guide member 1200 approach each other or move away from each other.

In the intervertebral fusion cage 1000 according to one embodiment of the present invention, the housing 1120 may include a housing body 1121, a screw head arrangement portion 1122, a threshold torque setting member arrangement portion 1123, a separation preventing member arrangement portion 1124, a guide hole 1125, a first connecting portion 1126, and a plate portion 1127.

The housing body 1121 has the shape of a box that is vertically penetrated. The vertically penetrated portion of the housing body 1121 may be filled with a bone graft material. A left-right width of the housing body 1121 may correspond to a left-right width of a vertically penetrated portion of a guide body 1210 of the guide member 1200 which will be described below.

The screw head arrangement portion 1122 is formed to pass through the housing body 1121 in a front-rear direction. More specifically, the screw head arrangement portion 1122 is formed to pass through a front wall 1121a of the housing body 1121 in the front-rear direction. In a state in which the screw head 1111 is disposed at the screw head arrangement portion 1122, the screw body 1112 may protrude to the front of the housing body 1121.

The threshold torque setting member arrangement portion 1123 is formed in the housing body 1121 for the threshold torque setting member 1130 to be disposed therein. More specifically, the threshold torque setting member arrangement portion 1123 may be formed at the front wall 1121a of the housing body 1121. In one embodiment of the present invention, the threshold torque setting member arrangement portion 1123 is formed to surround the screw head arrangement portion 1122 in the circumferential direction. Also, the threshold torque setting member arrangement portion 1123 has the shape of a slot passing through both sides of the housing body 1121 for the threshold torque setting member 1130 to be disposed to pass through a side surface of the front wall 1121*a* of the housing body 1121.

The separation preventing member arrangement portion 1124 is formed in the housing body 1121 for the separation preventing member 1140 to be disposed therein. In one embodiment of the present invention, the separation preventing member arrangement portion 1124 is formed as a through-hole passing through both sides of the housing body 1121. More specifically, the separation preventing member arrangement portion 1124 passes through both sides of the front wall 1121*a* of the housing body 1121, and at least a portion of the separation preventing member 1140 is formed to be inserted into the second groove 1111*c* of the screw head 1111.

The guide hole 1125 is formed to pass through a rear wall 1121*b* of the housing body 1121 in the front-rear direction to allow a driving tool (not illustrated) for rotating the screw to pass through the vertically penetrated portion of the housing body 1121 and reach the screw head 1111. The driving tool may reach the screw head 1111 through the guide hole 1125.

The first connecting portion 1126 is formed at the housing body 1121 for the plate 1300 to be movably connected in the vertical direction. In one embodiment of the present invention, the first connecting portion 1126 is provided at left and right sidewalls 1121*c* of the housing body 1121. The first connecting portion 1126 is engaged with a second connecting portion 1340 of the plate 1300 which will be described below. For example, the first connecting portion 1126 may include a shape of a groove recessed in the vertical direction.

The plate portion 1127 is connected to a lower side of the housing body 1121. The plate portion 1127 may be disposed opposite to the plate 1300 which will be described below. The plate portion 1127 may extend to the front, rear, and both sides of the housing body 1121. Accordingly, the plate portion 1127 may form a lower surface of the intervertebral fusion cage 1000. Meanwhile, a central portion of the plate portion 1127 may have a vertically penetrated form to communicate with the vertically penetrated portion of the housing body 1121. Also, at both sides of the plate portion 1127, a guide groove 1127*a* may be provided from a corner toward the threshold torque setting member arrangement portion 1123 to guide insertion of the threshold torque setting member 1130 into the threshold torque setting member arrangement portion 1123.

The threshold torque setting member 1130 is disposed in the housing 1120, prevents rotation of the screw head 1111 with torque less than a threshold torque set on the screw head 1111, and allows the rotation of the screw head 1111 in a case where torque greater than or equal to the threshold torque is applied. In one embodiment of the present invention, the threshold torque setting member 1130 may, while inserted into the first grooves 1111*a* of the screw head 1111, suppress the rotation of the screw head 1111 before the set threshold torque is applied and may be separated from the first grooves 1111*a* and allow the rotation of the screw head 1111 due to the first protruding portion 1111*b* adjacent thereto in the case where the torque greater than or equal to the threshold torque is applied.

The threshold torque setting member 1130 may include a member body 1131 disposed to surround at least a portion of a circumference of the screw head 1111 and a catching portion 1132 protruding from the member body 1131 toward the screw head 1111 in order to be inserted into the first grooves 1111*a*. For example, the member body 1131 may be disposed to surround about half of the screw head 1111 in the circumferential direction thereof, and the catching portion 1132 may protrude from one side end of the member body 1131 toward the screw head 1111. In relation to this, in the case where the torque greater than or equal to the threshold torque is applied to the screw 1110, the member body 1131 may be elastically deformed.

The separation preventing member 1140 is disposed to be fixed to the housing 1120 while inserted into one portion of the second groove 1111*c* and prevents the screw 1110 from being separated from the housing 1120. In one embodiment of the present invention, the separation preventing member 1140 may be formed in the shape of a pin. More specifically, in a state in which the separation preventing member 1140 is inserted into the separation preventing member arrangement portion 1124 formed as the through-hole passing through both sides of the housing body 1121, at least a portion of the separation preventing member 1140 may be inserted into the second groove 1111*c* of the screw head 1111. Also, the separation preventing member 1140 may be disposed perpendicular to the screw 1110.

Figure 8:
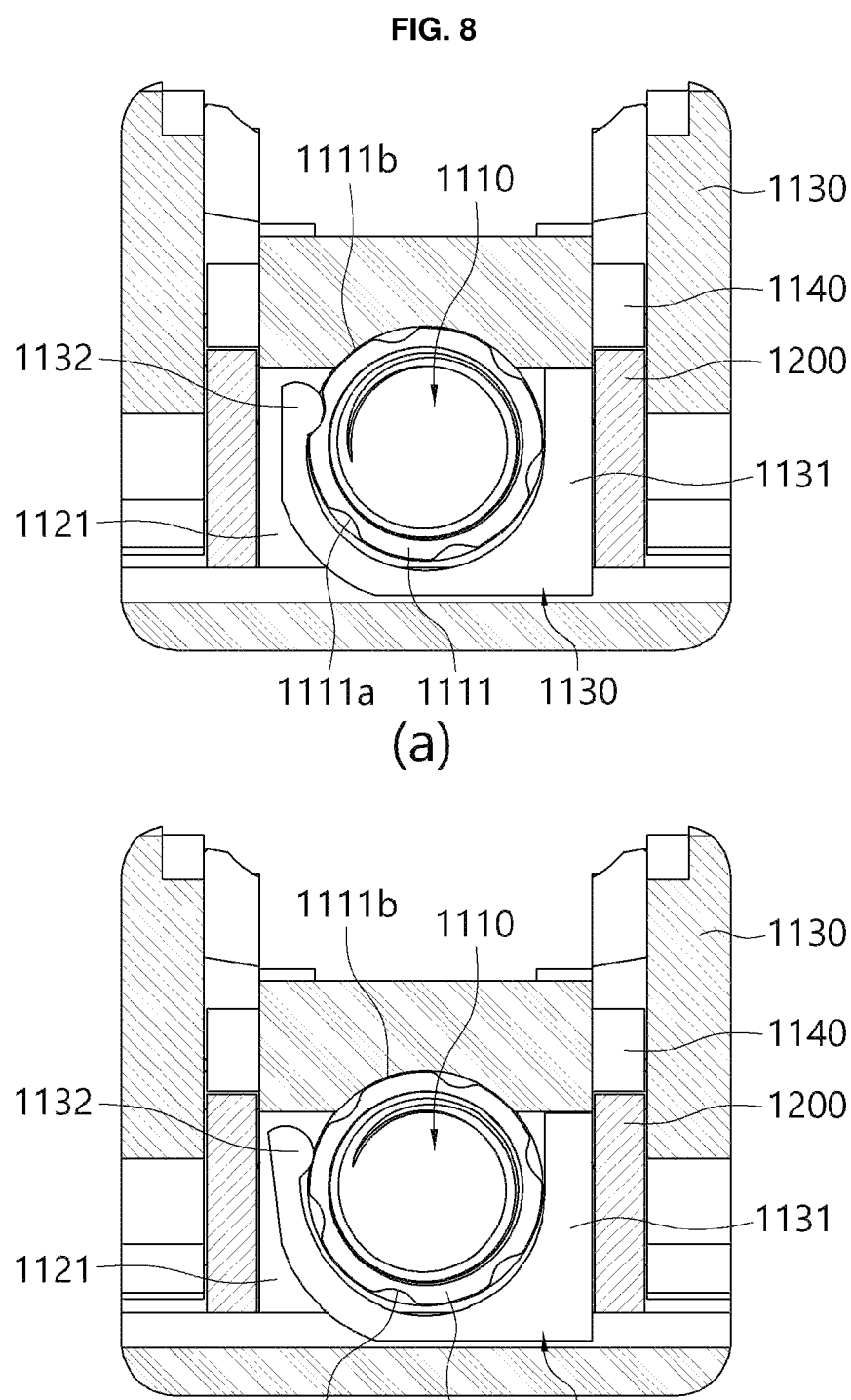
FIG. 8 is a view illustrating a driving state of a screw driving module of the intervertebral fusion cage according to one embodiment of the present invention.

FIG. 8 is a view illustrating a driving state of the screw driving module of the intervertebral fusion cage according to one embodiment of the present invention.

Referring to FIG. 8, in a state in which the catching portion 1132 of the threshold torque setting member 1130 is inserted into the first grooves 1111*a*, the rotation of the screw 1110 is limited by the catching portion 1132 before the torque greater than or equal to the threshold torque is applied. This is because the first protruding portion 1111*b* adjacent to the first grooves 1111*a*, into which the catching portion 1132 is inserted, is caught at the catching portion 1132 and suppresses the rotation of the screw. Meanwhile, in the case where the torque greater than or equal to the threshold torque is applied to the screw 1110, the first protruding portion 1111*b* of the screw head 1111 pushes the catching portion 1132 radially outward from the first grooves 1111*a*. Accordingly, as the screw head 1111 rotates, the screw 1110 rotates. The guide member 1200 engaged with the screw 1110 may move according to the rotation of the screw 1110.

The screw body 1112 of the screw 1110 is screw-rotatably coupled to the guide member 1200. The guide member 1200 is displaced forward or rearward while moving relative to the screw driving module 1100, and displacement of the plate 1300 occurs according to changes in positions of the guide member 1200 and the screw driving module 1100 relative to each other. The guide member 1200 may include a guide body 1210, a front guide portion 1220, a rear guide portion 1230, a screw hole 1240, and a rear hole 1250.

The guide body 1210 is formed to be vertically penetrated. The guide body 1210 may have the shape of a frame whose central portion is penetrated. Also, the guide body 1210 may have a quadrangular shape as a whole. The housing body 1121 of the housing 1120 of the screw driving module 1100 is disposed inside the guide body 1210, and according to rotation of the screw 1110 rotatably coupled to the housing 1120, the housing 1120 moves relative to the guide member 1200 in the guide body 1210. As described above, the vertically penetrated portion of the guide body 1210 may have a left-right width that corresponds to the left-right width of the housing body 1121 of the screw driving module 1100.

The front guide portion 1220 is formed to be inclined at a front portion of the guide body 1210. During the displacement of the guide member 1200, the front guide portion 1220 guides a front guided portion 1320 of the plate 1300 and guides lifting of a front portion of the plate 1300. In one embodiment of the present invention, the front guide portion 1220 protrudes to both sides from a sidewall of the front portion of the guide body 1210 and is formed with a predetermined angle to be inclined downward from the rear toward the front.

The rear guide portion 1230 is formed to be inclined at a rear portion of the guide body 1210. During the displacement of the guide member 1200, the rear guide portion 1230 guides a rear guided portion 1330 of the plate 1300. In other words, lifting of a rear portion of the plate 1300 is guided by the rear guide portion 1230. In one embodiment of the present invention, the rear guide portion 1230 protrudes to both sides from a sidewall of the rear portion of the guide body 1210 and is formed with a predetermined angle to be inclined downward from the rear toward the front.

The screw hole 1240 may be formed at a front of the guide body 1210. The screw hole 1240 may be formed by passing through the front sidewall of the guide body 1210 in the front-rear direction. The screw body 1112 of the screw 1110 of the screw driving module 1100 disposed in the guide body 1210 may be disposed to be engaged with the screw hole 1240. Accordingly, during the driving of the screw 1110, the guide member 1200 may move forward or rearward relative to the housing 1120 of the screw driving module 1100.

The rear hole 1250 is formed at a rear of the guide body 1210 and communicates with the guide body 1210. More specifically, the rear hole 1250 may be formed by passing through the rear sidewall of the guide body 1210 in the front-rear direction. The rear hole 1250 allows the driving tool for driving the screw 1110 of the screw driving module 1100 to enter the guide body 1210. The driving tool that has entered the guide body 1210 through the rear hole 1250 may pass through the guide hole 1125 of the housing 1120 and reach the screw 1110.

The plate 1300 is movably connected to the housing 1120 and is displaced according to relative movement between the screw driving module 1100 and the guide member 1200. During the rotation of the screw 1110, the screw driving module 1100 moves forward or rearward relative to the guide member 1200, and the plate 1300 may be displaced due to the guide member 1200. Here, the displacement of the plate 1300 may indicate upward or downward movement of a portion of the plate 1300 or the entire plate 1300.

The plate 1300 may form the lordosis and height of the intervertebral fusion cage 1000. In one embodiment of the present invention, the plate 1300 forms an upper surface of the intervertebral fusion cage 1000. The plate 1300 may include a plate body 1310, the front guided portion 1320, the rear guided portion 1330, and the second connecting portion 1340.

The plate body 1310 has a quadrangular shape as a whole and is penetrated in the vertical direction. The plate body 1310 has sidewalls, which extend downward, formed at four sides of the penetrated portion.

The front guided portion 1320 is guided by the front guide portion 1220 of the guide member 1200. The front portion of the plate 1300 may be lifted when the plate 1300 moves relative to the guide member 1200, and the front guided portion 1320 is guided by the front guide portion 1220. In one embodiment of the present invention, the front guided portion 1320 is formed to be recessed in an inner side surface of both sidewalls of the plate body 1310 and is formed to be recessed to be inclined downward from the rear toward the front.

The rear guided portion 1330 is guided by the rear guide portion 1230 of the guide member 1200. The rear portion of the plate 1300 may be lifted when the plate 1300 moves relative to the guide member 1200, and the rear guided portion 1330 is guided by the rear guide portion 1230. In one embodiment of the present invention, the rear guided portion 1330 is provided at a rear sidewall of the plate body 1310 and is formed to be inclined downward from the rear toward the front.

The second connecting portion 1340 is movably connected to the first connecting portion 1126 in the vertical direction. The second connecting portion 1340 connects the plate 1300 to the housing 1120 of the screw driving module 1100. In one embodiment of the present invention, the second connecting portion 1340 may be movably connected to the first connecting portion 1126 of the housing 1120 in the vertical direction. In one embodiment of the present invention, the second connecting portion 1340 may include a portion protruding from an inner side surface of both sidewalls of the plate body 1310 and extending in the vertical direction.

Hereinafter, an operation of the intervertebral fusion cage 1000 according to one embodiment of the present invention will be described.

Figure 9:
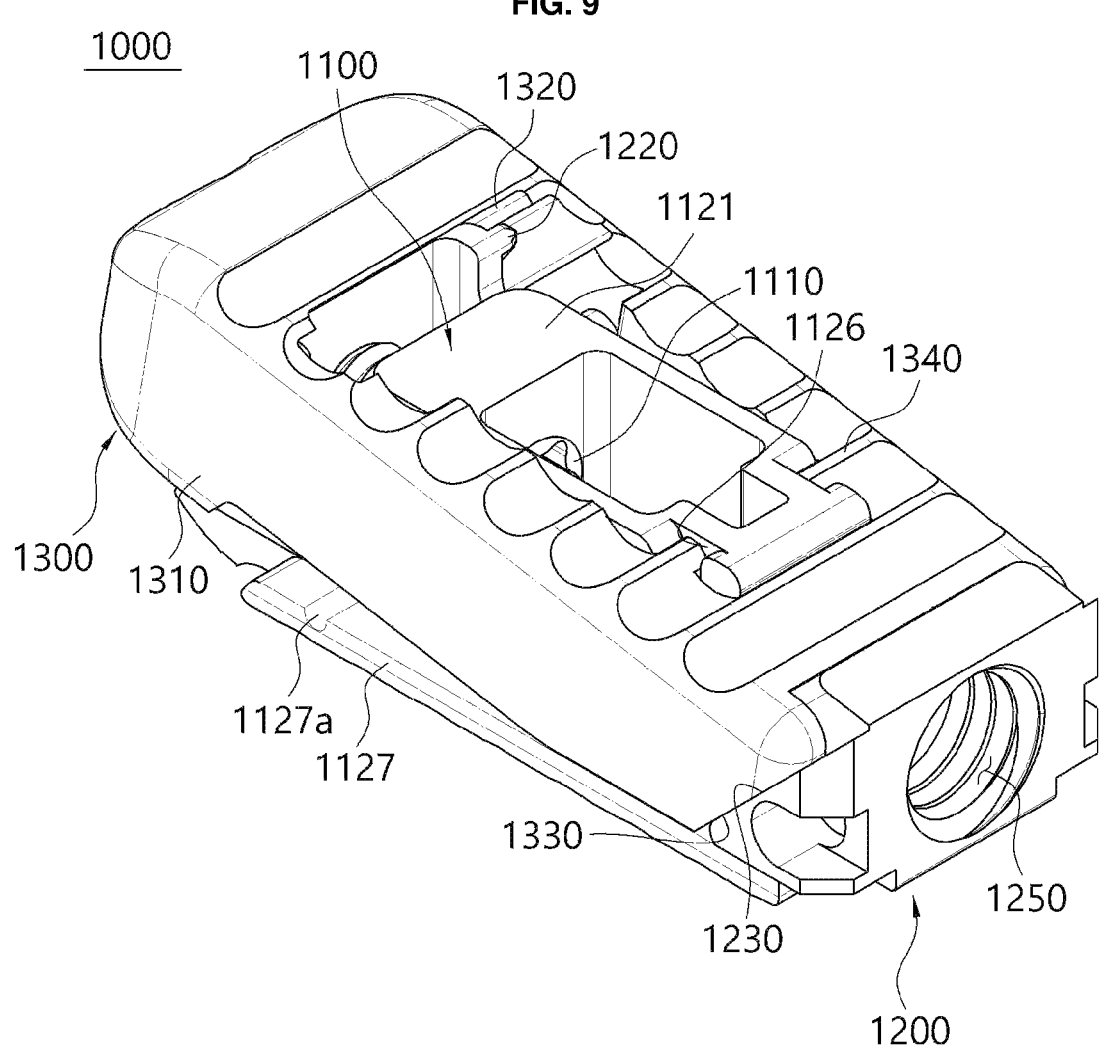
FIG. 9 is a perspective view of a state in which an angle of a plate of the intervertebral fusion cage according to one embodiment of the present invention is expanded.

FIG. 9 is a perspective view of a state in which an angle of the plate of the intervertebral fusion cage according to one embodiment of the present invention is expanded. Also, FIG. 10 is a lateral view of the state in which the angle of the plate of the intervertebral fusion cage according to one embodiment of the present invention is expanded, and FIG. 11 is a lateral cross-sectional view showing a process in which angles of the front guide portion and the front guided portion of the intervertebral fusion cage according to one embodiment of the present invention are matched.

Figure 10:
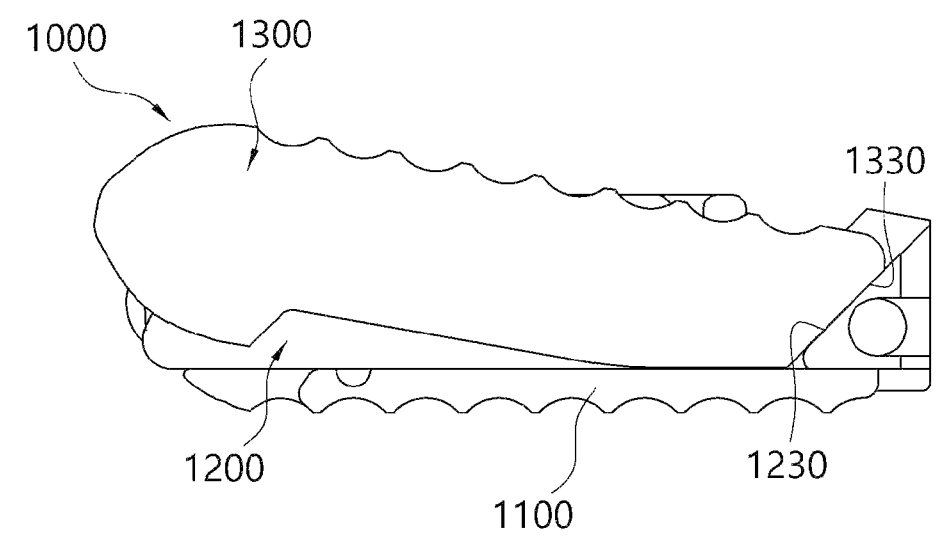
FIG. 10 is a lateral view of the state in which the angle of the plate of the intervertebral fusion cage according to one embodiment of the present invention is expanded.
Figure 11:
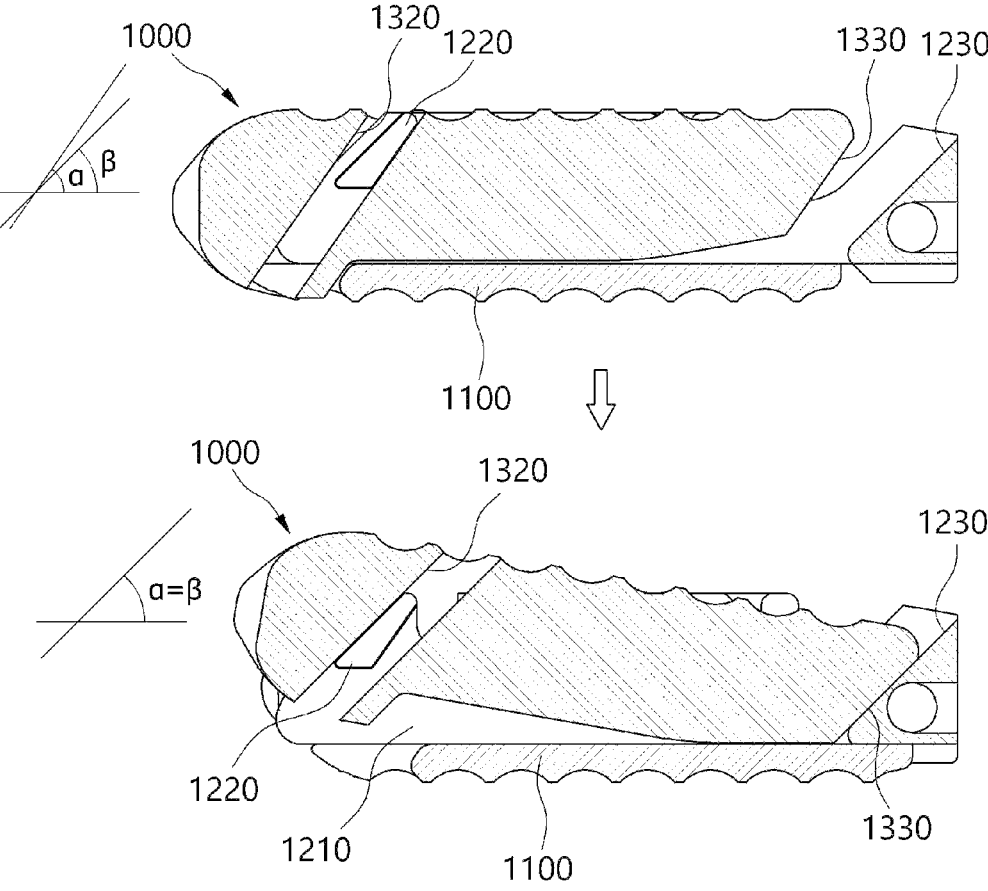
FIG. 11 is a lateral cross-sectional view showing a process in which angles of a front guide portion and a front guided portion of the intervertebral fusion cage according to one embodiment of the present invention are matched.

Referring to FIGS. 9 to 11, when the screw 1110 of the screw driving module 1100 rotates in one direction in a state in which the plate 1300 is not expanded relative to the guide member 1200, the guide member 1200 moves forward relative to the screw driving module 1100, and the plate 1300 is displaced. Here, first, the front portion of the plate 1300 is moved in the vertical direction, and an angle formed between the plate 1300 and the guide member 1200 increases. In relation to this, the rotation of the screw 1110 may occur when torque greater than or equal to the threshold torque is applied to the screw.

As illustrated in FIG. 11, the angle of the front portion of the plate 1300 is expanded until an angle α between the front guided portion 1320 of the plate 1300 and the ground and an angle β between the front guide portion 1220 of the guide member 1200 and the ground become equal to each other. In a state in which the plate 1300 is not expanded, the angle β between the front guide portion 1220 and the ground is formed to be smaller than the angle α between the front guided portion 1320 of the plate 1300 and the ground. Accordingly, during the displacement of the plate 1300, the front portion of the plate 1300 may be lifted until the angle between the front guide portion 1220 and the ground and the angle between the front guided portion 1320 and the ground become equal to each other, and lordosis expansion may occur. In other words, the angle β between the front guide portion 1220 and the ground may correspond to lordosis of the spine that the intervertebral fusion cage 1000 may provide. Meanwhile, as the plate 1300 moves rearward relative to the guide member 1200 in addition to the front portion of the plate 1300 being lifted, the rear guided portion 1330 of the plate 1300 and the rear guide portion 1230 of the guide member 1200 come in contact with each other.

In this way, at an early stage of the displacement of the plate 1300, the front portion of the plate 1300 is lifted until the angle between the front guide portion 1220 and the ground and the angle between the front guided portion 1320 and the ground become equal to each other. As a result, lordosis expansion may occur. Through such a process, the intervertebral fusion cage 1000 may, while inserted into an intervertebral space of a patient, allow lordosis of the spine to have a predetermined angle.

Figure 12:
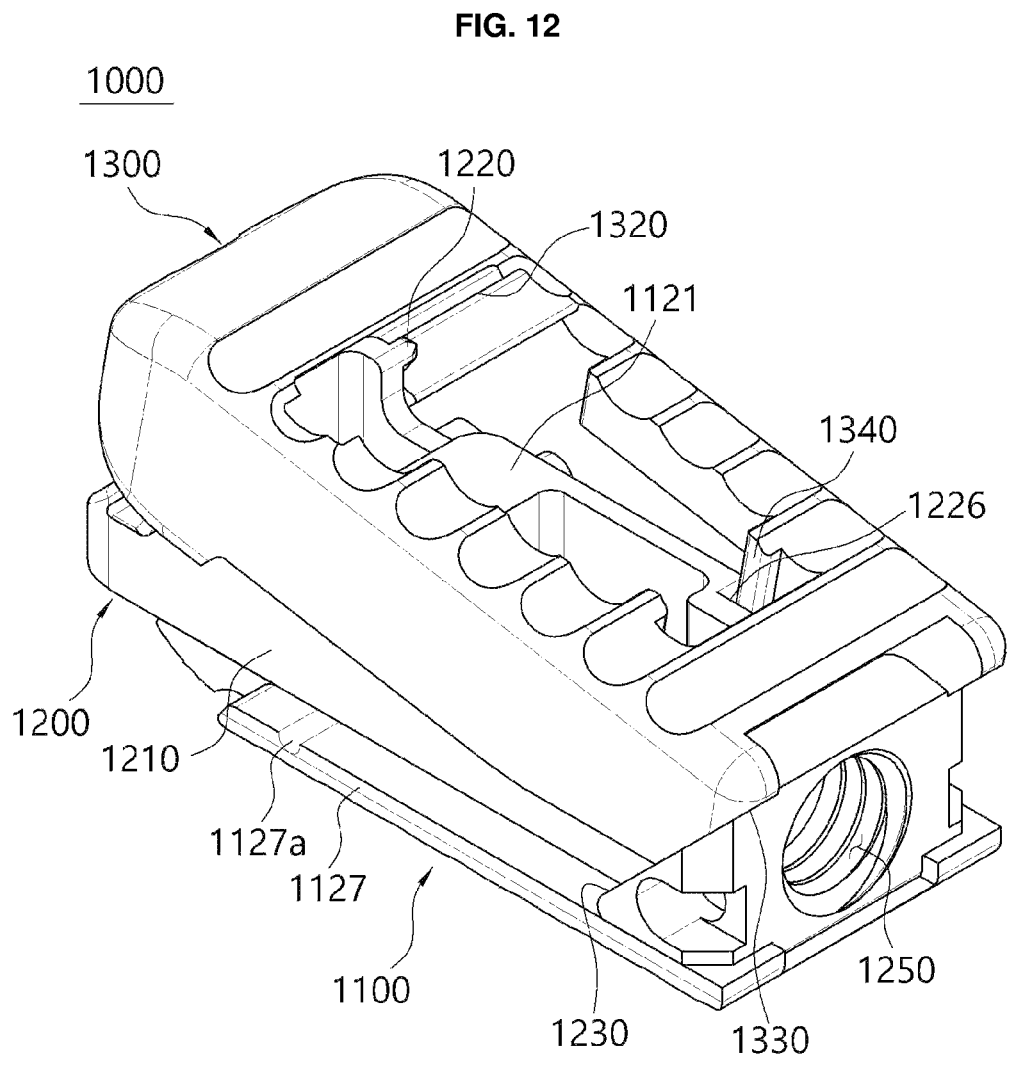

FIG. 12 is a perspective view of a state in which a height of the plate of the intervertebral fusion cage according to one embodiment of the present invention is increased after the angle of the plate is expanded. Also, FIG. 13 is a lateral view of the state in which the height of the plate of the intervertebral fusion cage according to one embodiment of the present invention is increased after the angle of the plate is expanded.

Figures 13, 14:
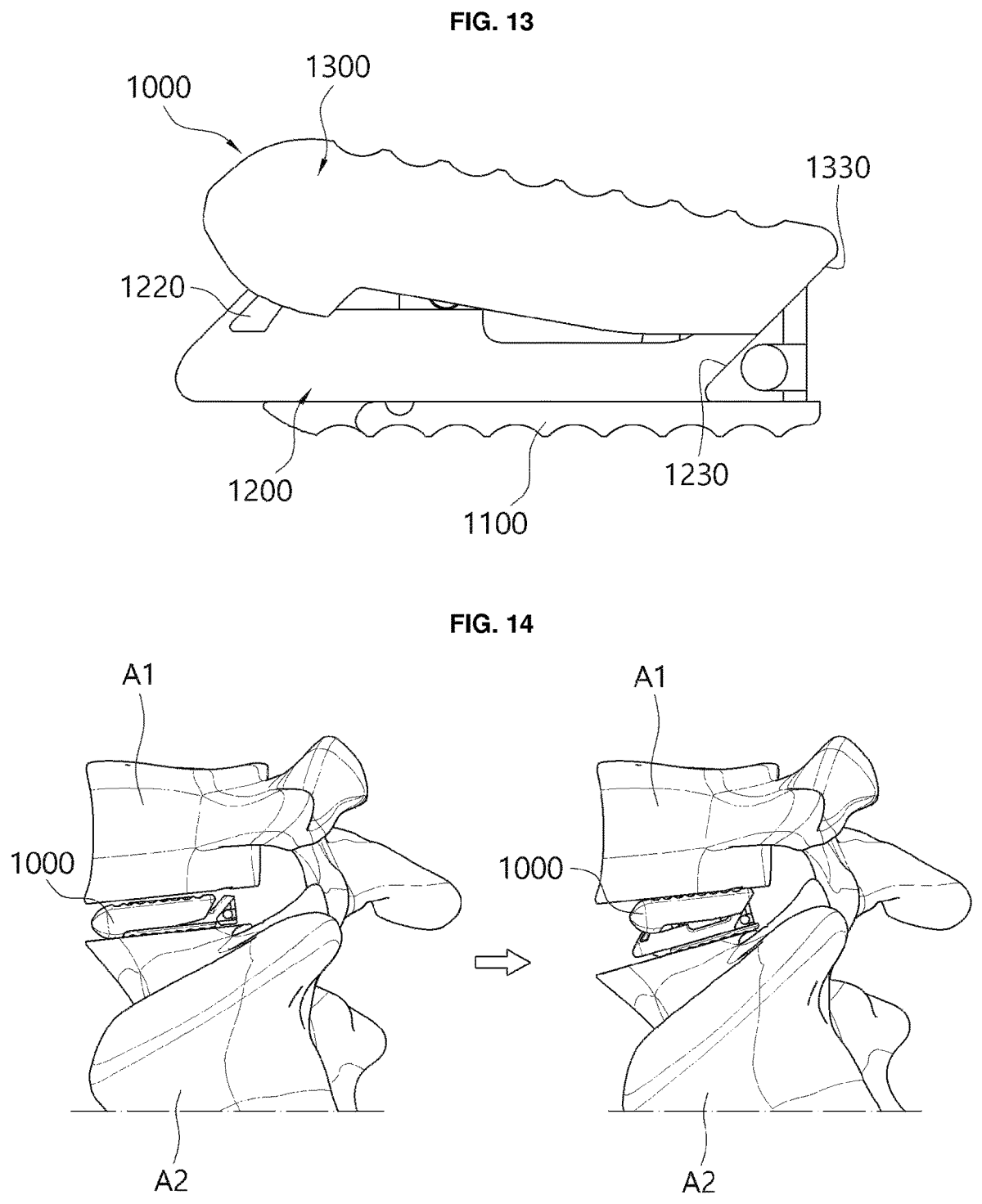

Referring to FIGS. 12 and 13, in a state in which the front portion of the plate 1300 is lifted as much as possible such that the angle between the front guided portion 1320 of the plate 1300 and the ground and the angle between the front guide portion 1220 of the guide member 1200 and the ground are equal to each other, and the rear guided portion 1330 of the plate 1300 and the rear guide portion 1230 of the guide member 1200 are in contact with each other, when the screw 1110 of the screw driving module 1100 further rotates in the one direction, the entire plate 1300 is moved in the vertical direction, and the height of the plate 1300 increases. That is, after the angle is increased by as much as the predetermined angle, when the screw 1110 further rotates, the guide member 1200 moves forward relative to the screw driving module 1100 in a state in which the front guided portion 1320 and the rear guided portion 1330 of the plate 1300 are in contact with the front guide portion 1220 and the rear guide portion 1230 of the guide member 1200, respectively, and the entire plate 1300 moves vertically upward. Accordingly, height expansion of the intervertebral fusion cage 1000 occurs. Here, the expansion height may be set to correspond to a height of an intervertebral space that the intervertebral fusion cage 1000 is meant to secure. In relation to this, the rotation of the screw 1110 may occur when torque greater than or equal to the threshold torque is applied to the screw.

The displacement of the intervertebral fusion cage 1000 according to one embodiment of the present invention is reversible. In other words, in a case where torque greater than or equal to the threshold torque is applied to the screw 1110 in the other direction in a state in which the intervertebral fusion cage 1000 is expanded, the above-described displacement of the guide member 1200 and the plate 1300 may occur in the reverse order.

Meanwhile, in relation to the relative movement between the screw driving module 1100 and the guide member 1200, the guide member 1200 may further have a side guide portion 1260 formed at both sidewalls of the guide body 1210 in the front-rear direction. Also, the separation preventing member 1140 may be disposed to pass through both sides of the housing 1120 and have one end and the other end seated on the side guide portion 1260.

In one embodiment of the present invention, the side guide portion 1260 may be provided as corners of upper ends of both sidewalls of the guide body 1210. Also, the one end and the other end of the pin-type separation preventing member 1140 may protrude to both sides of the housing 1120 and may be guided by the side guide portion 1260 when the screw driving module 1100 moves relative to the guide member 1200.

Figure 15:
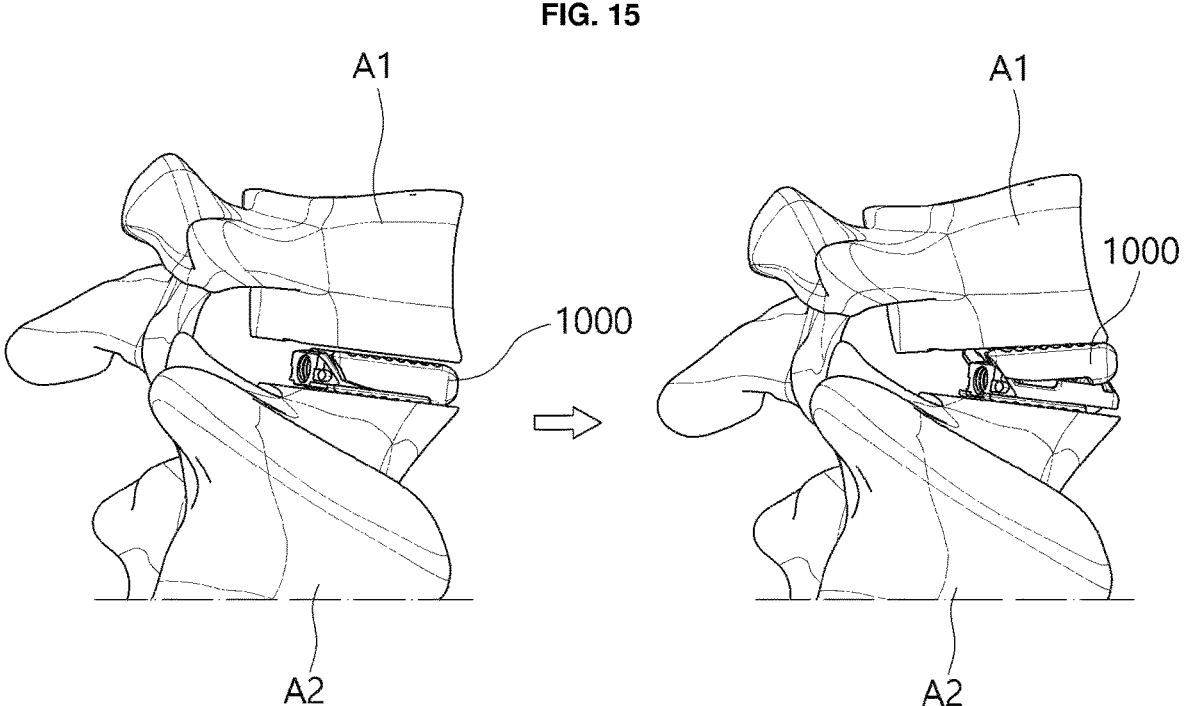
FIG. 15 is a view illustrating a process in which the intervertebral fusion cage according to one embodiment of the present invention is used in transforaminal lumbar interbody fusion (TLIF).

FIG. 14 is a view illustrating a process in which the intervertebral fusion cage according to one embodiment of the present invention is used in posterior lumbar interbody fusion (PLIF). FIG. 15 is a view illustrating a process in which the intervertebral fusion cage according to one embodiment of the present invention is used in transforaminal lumbar interbody fusion (TLIF).

Referring to FIGS. 14 and 15, the intervertebral fusion cage 1000 according to one embodiment of the present invention may be used for both PLIF and TLIF. The intervertebral fusion cage 1000 is inserted into a space between an upper vertebra A1 and a lower vertebra A2 to expand both lordosis and height. Also, by being expanded after being inserted into the patient's body, the intervertebral fusion cage 1000 enables minimally invasive surgery when inserted.

Embodiments of the present invention have been described above, but the spirit of the present invention is not limited by the embodiments presented herein. Those of ordinary skill in the art who understand the spirit of the present invention may easily propose other embodiments by adding other components, changing components, or omitting components within the scope of the same spirit. However, such embodiments also belong to the scope of the spirit of the present invention.

The invention claimed is:

1. An intervertebral fusion cage comprising:
a screw driving module including a screw including a screw head and a screw body extending from the screw head and having screw threads on an outer circumferential surface thereof, a housing in which the screw head is rotatably accommodated, and a threshold torque setting member disposed in the housing and configured to prevent rotation of the screw head with torque less than a threshold torque set on the screw head and allow the rotation of the screw head in a case where torque greater than or equal to the threshold torque is applied;
a guide member to which the screw body of the screw is screw-rotatably coupled; and
a plate movably connected to the housing and configured to be displaced according to relative movement between the screw driving module and the guide member,
wherein, during rotation of the screw, the screw driving module moves forward or rearward relative to the guide member, and the plate is displaced due to the guide member,
wherein the screw head has one or more first grooves on an outer circumferential surface thereof,
wherein, while inserted into the first grooves of the screw head, the threshold torque setting member prevents the rotation of the screw head before the set threshold torque is applied, and in the case where the torque greater than or equal to the threshold torque is applied, the threshold torque setting member is separated from the first grooves and allows the rotation of the screw head,
wherein the threshold torque setting member includes a member body disposed to surround at least a portion of a circumference of the screw head and a catching portion protruding from the member body toward the screw head in order to be inserted into the first grooves and in the case where the torque greater than or equal to the threshold torque is applied to the screw, the member body is elastically deformed so that the catching portion is separated from the first groove, wherein the guide member has a guide body formed to be vertically penetrated, wherein the screw driving module is disposed in the guide body, wherein the screw head further includes a second groove continuously recessed in the circumferential direction, wherein the screw driving module further comprises a separation preventing member disposed to be fixed to the housing while inserted into one portion of the second groove and configured to prevent the screw from being separated from the housing, wherein the separation preventing member is formed in the shape of a pin and is disposed perpendicular to the screw, wherein the guide body includes two sidewalls, wherein the guide member further has side guide portions formed at both sidewalls of the guide body in a front-rear direction, and wherein the separation preventing member is disposed to pass through both sides of the housing and has one end and the other end seated on the side guide portions, respectively.

2. The intervertebral fusion cage of claim 1, wherein:

the guide member has a screw hole formed at a front thereof, and the screw body of the screw is screw-coupled to the screw hole.

3. The intervertebral fusion cage of claim 1, wherein:

the guide member further has a rear hole formed to be penetrated at a rear thereof and communicating with the guide body; and a driving tool passing through the rear hole is able to reach the screw head.

4. The intervertebral fusion cage of claim 1, wherein the housing has a first connecting portion formed in a vertical direction, and the plate has a second connecting portion movably connected to the first connecting portion in the vertical direction.

5. The intervertebral fusion cage of claim 1, wherein the first grooves are formed in a longitudinal direction of the screw.

6. The intervertebral fusion cage of claim 5, wherein a plurality of the first grooves are disposed at predetermined intervals in a circumferential direction of the screw head.

* * * * *